(12) United States Patent
Klink et al.

(10) Patent No.: US 8,403,483 B2
(45) Date of Patent: *Mar. 26, 2013

(54) IMPLANTABLE SYSTEM FOR DETERMINING THE ACCOMMODATION REQUIREMENT BY OPTICAL MEASUREMENT OF THE PUPIL DIAMETER AND THE SURROUNDING LUMINANCE

(75) Inventors: Simon Klink, Stuttgart (DE); Georg Bretthauer, Karlsruhe (DE); Rudolf Guthoff, Rostock (DE); Ulrich Gengenbach, Remchingen (DE); Mark Bergemann, Göppingen (DE); Torsten Koker, Stutensee (DE); Wolfgang Rückert, Wülfrath (DE)

(73) Assignees: Forschungszentrum Karlsruhe GmbH, Karlsruhe (DE); Universitat Rostock, Rostock (DE)

( * ) Notice: Subject to any disclaimer, the term of this patent is extended or adjusted under 35 U.S.C. 154(b) by 191 days.

This patent is subject to a terminal disclaimer.

(21) Appl. No.: 12/449,618

(22) PCT Filed: Feb. 18, 2008

(86) PCT No.: PCT/EP2008/051937
§ 371 (c)(1),
(2), (4) Date: Jan. 27, 2011

(87) PCT Pub. No.: WO2008/101897
PCT Pub. Date: Aug. 28, 2008

(65) Prior Publication Data
US 2011/0109878 A1 May 12, 2011

(30) Foreign Application Priority Data
Feb. 21, 2007 (DE) .......... 10 2007 008 375

(51) Int. Cl.
A61B 3/14 (2006.01)
(52) U.S. Cl. .......... 351/209; 351/208; 351/206; 351/210
(58) Field of Classification Search .......... 351/200–246
See application file for complete search history.

(56) References Cited

U.S. PATENT DOCUMENTS

| | | | |
|---|---|---|---|
| 4,373,218 A | 2/1983 | Schachar | |
| 6,139,577 A * | 10/2000 | Schleipman et al. | 623/6.64 |
| 6,638,304 B2 | 10/2003 | Azar | |
| 2010/0324408 A1 * | 12/2010 | Klink et al. | 600/409 |

FOREIGN PATENT DOCUMENTS

| | | |
|---|---|---|
| CA | 2 313 693 | 1/2001 |
| DE | 102005038542 | 2/2007 |
| WO | 02/085245 | 10/2002 |
| WO | 2004/073547 | 9/2004 |

* cited by examiner

Primary Examiner — Mohammed Hasan
(74) Attorney, Agent, or Firm — Lucas & Mercanti, LLP; Klaus P. Stoffel

(57) ABSTRACT

An implantable system for determining the accommodation requirement in an artificial accommodation system by optical measurement of the pupil diameter and the surrounding luminance, including at least one optical system, at least one data acquisition system that does not contact the ciliary muscle and measures a diameter of the pupil and luminance around at least one eye as a physical control signal for the accommodation requirement, at least one data processing system for generating an actuating signal for the optical system from the detected physical control signals or for the purpose of switching to the standby mode, at least one energy supply system, and at least one fixing system. The system has one sensor or a plurality of sensors with sensor elements for measuring the pupil diameter and the surrounding luminance.

12 Claims, 2 Drawing Sheets

IMPLANTABLE SYSTEM FOR DETERMINING THE ACCOMMODATION REQUIREMENT BY OPTICAL MEASUREMENT OF THE PUPIL DIAMETER AND THE SURROUNDING LUMINANCE

The present application is a 371 of International application PCT/EP2008/051937 filed Feb. 18, 2008, which claims priority of DE 10 2007 008 375.2, filed Feb. 21, 2007, the priority of these applications is hereby claimed and these applications are incorporated herein by reference.

BACKGROUND OF THE INVENTION

The present application claims the priority of 10 2007 008 375.2-55. The priority document is incorporated by reference in its entirety in the present disclosure.

The subject matter of the invention is an implantable system for determining the accommodation requirement in an artificial accommodation system by optical measurement of the pupil diameter and the surrounding luminance, and the use thereof to restore the accommodative capacity.

The human eye is an optical system which uses a number of refractive interfaces to image focused objects on the retina. In the process, the light waves pass the cornea, the aqueous humor in the anterior chamber of the eye (camera anterior bulbi), the lens (lens crystallina) and the vitreous humor in the posterior segment of eyeball (camera vitrea bulbi), all of which have different refractive indices. If the object distance of the observed object changes, the imaging behavior of the optical system has to change in order to maintain an unchanging focused image on the retina. The human eye implements this by deforming the lens using the ciliary muscle (musculus ciliaris); as a result of this the shape and position of the front and rear sides of the lens basically change (accommodation). In the case of an intact accommodation system in a youthful person, the dioptric power of the system can vary by 14 dpt (breadth of accommodation) between the distance setting (desaccommodated state) and close-up setting (accommodated state). As a result, a youthful person with normal vision (emmetropia) is able to image focused objects on the retina, the objects lying between a far point at infinity and a near point approximately 7 cm in front of the cornea.

Since the ability of the human eye to accommodate reduces with increasing age, a number of artificially implantable lens systems with a variable focus have been developed.

Potentially accommodative intraocular lenses are lenses or lens systems which are inserted in place of the natural lens after the latter has been surgically removed and which are predominantly attached in the capsular bag. Haptics is intended to be applied to axially displace the lens by using a weak residual contraction of the ciliary muscle which is still available.

By way of example, DE 101 55 345 C2, U.S. Pat. No. 6,638,304 B2, WO 03/017873 A1 and U.S. Pat. No. 4,373, 218, DE 94 22 429 U1, DE 201 11 320 U1, DE 100 62 218 A1, DE 10139027, WO 02/083033, DE 10125829 A1, US 2004/0181279A1, US2002/0149743, U.S. Pat. No. 6,120,538, U.S. Pat. No. 6,120,538, DE 10155345 C2, U.S. Pat. No. 6,096, 078, U.S. Pat. No. 6,638,304, U.S. Pat. No. 6,638,304 and WO004605 all disclose apparatuses for restoring the accommodative capacity.

Furthermore, there are a number of scientific publications relating to the accommodative capacity of lens systems. Reference is made in an exemplary manner to the following publications:

Schneider, H.; Stachs, O.; Guthoff, R.: Evidenzbasierte Betrachtungen zu akkommodativen Kunstlinsen [Evidence-based observations on accommodative artificial lenses], 102. Jahrestagung der Deutschen Ophthalmologischen Gesellschaft [102nd Annual convention of the German Ophthalmological Society] (Berlin, Germany, Sep. 23-26, 2004) (2004)); Kammann, J.; Dornbach, G.: Empirical results regarding accommodative lenses. In: Current Aspects of Human Accomodation. Eds.: Guthoff, R.; Ludwig, K. Kaden Verlag Heidelberg (2001) 163-170, Fine, H.; Packer M.; Hoffmann R.: Technology generates IOL with amplitude of accommodation" (Ophthalmology Times Special Report, Mar. 15, 2005) (2005), Lavin, M.: Multifocal intraocular lenses—part 1. Optometry Today May 2001 (2001) 34-37; Lavin, M.: Multifocal intraocular lenses—part 2. Optometry Today August 2001 (2001) 43-44. Nishi, O.; Nishi, K.; Mano, C.; Ichihara, M.; Honda, T.: Controlling the capsular shape in lens refilling. Archives of Ophthalmology 115(4) (1997) 507-510; Fine, I. H.: The SmartLens—a fabulous new IOL technology. Eye World 7(10) (2002).

Overall, it should be noted that, in principle, the artificial lens implanted during a cataract extraction is unable to focus to different distances. Nor do these operations solve the problem of the human eye no longer being able to sufficiently accommodate to a reading distance of approximately 30 cm once it reaches an age of approximately 45 years. Biological reasons mean that previous attempts of utilizing intraocular structures, in particular the ciliary muscle activity, to mechanically change the refraction of implantable systems have up until now been unsuccessful. Nor is this to be expected in the medium term.

A method of determining the accommodation requirement is to measure the pupil diameter and the surrounding luminance. U.S. Pat. No. 6,638,304 B2 discloses options for measuring the luminance and pupil diameter. In the process, a photosensor measures the luminance, and an electrode which detects changes in the potential of the iris measures the pupil diameter.

Furthermore, so-called pupilometers are known which can measure the pupil diameter optically. Said pupilometers usually emit infrared radiation and detect the reflected light; the pupil diameter can be estimated as a result of this.

However, currently available pupilometers are large and heavy. This means that they are completely unsuitable for being implanted. Furthermore, the image processor for detecting and measuring the pupil requires high computational power.

Using an electrode in the muscle of the iris brings about uncertainties with respect to tissue changes. If the electrode is encapsulated by the tissue, it is no longer possible to measure a sufficient signal. Moreover, this requires additional complexity and a previously unpredictable risk during the implantation.

SUMMARY OF THE INVENTION

Using this as a starting point, it is the object of the present invention to propose an implantable accommodation system which is implanted into the capsular bag and which obtains its control impulses independently of the ciliary body activity.

This object is achieved by an implantable system for determining the accommodation requirement in an artificial accommodation system by optical measurement of the pupil diameter and the surrounding luminance, comprising
 a) at least one optical system,
 b) at least one data acquisition system which does not contact the ciliary muscle and has means for measuring a diameter of the pupil and luminance around at least one eye as a physical control signal for the accommodation requirement, c) at least one data processing system for generating an actuating signal for the optical system from the detected physical control signals or for the purpose of switching to the stand-by mode, d) at least one energy supply system, and e) at least one fixing system, wherein the system has one sensor or a plurality of sensors with sensor elements for optically measuring the pupil diameter and the surrounding luminance.

Such an accommodation system with features a)-e) is, for example, described in the German patent application 102005038542 which was not published before the priory date of the current application. Accordingly, the individual systems are connected to form one or more control circuits. The optical system, the data acquisition system, the data processing system, the energy supply system and the fixing system are preferably combined to form an implant which can be inserted to restore the accommodative capacity of the animal or human eye using the fixing system. Here, the optical system is arranged in the beam path of the eye and, in conjunction therewith, forms the dioptric apparatus of the eye. In a similar fashion, the data acquisition system, the data processing system and the energy supply system are preferably arranged outside of the beam path.

The optical system, which comprises one or more active-optical elements and/or one or more rigid lenses which can be displaced axially by actuators (=passive-optical elements), is intended to influence the imaging behavior in the beam path. It has to be transparent in the visible wavelength range and must be able to change, over time, the position and/or the shape of at least one of its refractive interfaces in order to change the dioptric power of the dioptric apparatus. The actuating component in this case comprises energy actuators and energy transducers (Grote/Feldhusen (Eds.): Dubbel—Taschenbuch für den Maschinenbau. 21. Auflage. [Dubbel—Handbook for Engineering. 21st edition]. Springer Verlag Berlin Heidelberg New York (2005)); when actuating signals of a data processing unit act on said actuating component, forces are put into effect which can then be converted into motion.

In the case of a passive-optical element, an actuator axially displaces one or more rigid lenses in the beam path. This operating principle is routinely used in technical products for focusing. By way of example, DE4300840A1 describes a vario-objective for compact cameras comprising two lens groups whose mutual relative distance can be varied to effect a change in the focal length.

The above-described object of an active-optical element can be achieved using different mechanisms. In the process, it is necessary to distinguish between a change in the refractive index distribution and a change in the curvature of an interface separating two media with different refractive indices. These changes can be implemented by different physical action principles which are discussed below.

Change in the refractive index by electro-optical materials: Electromagnetic fields can influence the birefringent property of electro-optical materials. This makes it possible to set a defined refractive index distribution which affords the possibility of influencing the imaging behavior in a polarization plane of the light in a targeted fashion. In addition to a targeted change of the position of the focus, this can also comprise correcting higher-order image defects (e.g. astigmatisms, spherical aberration, coma). Two such systems have to be arranged in succession and cross at right angles in order to equally influence both mutually orthogonal polarization planes. U.S. Pat. No. 6,619,799 describes the use of such an active-optical element in a glasses frame. In the process, two transparent electrode surfaces enclose the electro-optical layer and an electrical voltage can be applied between said electrode surfaces in order to change the radial refractive index profile. A desired refractive index profile can be obtained by either modulating the amplitude and frequency of the control voltage or by dividing the electrodes into a number of regions which are respectively supplied with different voltages.

Change in the refractive index by changing the density of a compressible fluid: The refractive index of a compressible fluid (e.g. a gas or a gas mixture) depends on its density. This dependence is described by the Gladstone-Dale constant. If the pressure and/or the temperature are varied in a gas-filled chamber which has one or more curved interfaces, the imaging behavior of the optical system also changes accordingly. U.S. Pat. No. 4,732,458 describes, for example, such an arrangement for a multi-lens element whose refractive power can be changed continuously. The pressure increase in the rigid, gas-filled chamber is effected by a displaceable piston which is guided in a cylinder and arranged away from the optical axis.

Change in geometry as a result of an external force acting on an elastic solid body: An elastic solid body whose refractive index differs from that of the surroundings can be deformed by external forces such that the curvature of its light refractive surfaces changes and, as a result, this influences the optical imaging behavior. U.S. Pat. No. 6,493,151 describes, for example, an arrangement of a homogeneously or inhomogeneously designed solid body which can be deformed in such a fashion onto which radial forces can be transferred by means of a ring with a variable diameter. Thermal means or magnetic/electric fields can change the diameter of the ring. DE4345070 describes, for example, an arrangement for a deformable shell-shaped solid body which is filled by a transparent liquid and whose light refractive surfaces are hydraulically or pneumatically deformed by a ring-shaped fluid actuator. DE10244312 mentions the change in the refractive power of an artificial deformable lens implanted into the eyeball as an application example for an actuator composed of buckypaper (paper-like network of carbon nanotubes).

Change in geometry as a result of influencing the wetting angle (electrowetting): Two mutually immiscible fluids with approximately the same density but different refractive indices form a spherically curved or planar interface (meniscus). If the one, electrically conductive fluid is brought into contact with an electrode and a potential difference is applied with respect to a second electrode separated from both fluids by a dielectric layer, then the so-called electrowetting effect can change the wetting angle, and hence the curvature of the meniscus. Since the meniscus separates two media with differing refractive indices, there is a change in the optical imaging behavior. WO99/18456 describes an axial arrangement of conductive fluid, transparent dielectric and transparent electrode in the beam path and also measures for radially centering the tear in the optical axis. WO03/069380 describes an arrangement in which the dielectric-coated electrode is arranged cylindrically around the optical axis. The electrically conductive fluid and the insulating fluid, as well as the meniscus separating the two, are arranged axially one behind the other in the optical axis.

Change in geometry as a result of changing the pressure of a fluid: If the pressure difference in a fluid-filled chamber, having one or more deformable interfaces, and its surroundings is changed, this results in a change in the curvature of the interfaces and, accordingly, in a change in the imaging behavior of the optical system as well. U.S. Pat. No. 4,466,706 describes such an arrangement in an exemplary fashion, with a displacement mechanism changing the pressure difference. Here, turning a screw located in the cylindrical shell displaces fluid which leads to a change in the curvature of the two end faces of the cylinder. Alternatively, the cylindrical shell can also be of a two-part design, with an axial relative movement of the two parts making a displacement effect possible.

Change in geometry as a result of force developing within a smart material: Smart materials can develop forces by changing their atomic/molecular structure and, as a result of this, they can deform. The optical imaging behavior can likewise be influenced accordingly by setting an interface profile between the smart material and the surroundings. US2004/0100704 describes, for example, a shape memory polymer used for this purpose, which is inserted within a deformable lens body as a phase or layer and can locally change the shape of the body when influenced by energy. The post-operative, nonreversible correction of the imaging behavior of implanted intraocular lenses is mentioned as an exemplary application. JP01230004 describes using a swelling gel and a solvent arranged in layers within a deformable solid body in an exemplary fashion. The application of a voltage can effect a change in the solubility of the solvent in the swelling gel such that the latter thereupon undergoes a change in volume. This changes the curvature of the refractive surface.

Combinations of the abovementioned active principles are also possible. It follows that the optical system can adjust the focal position of the dioptric apparatus. Moreover, the optical system can comprise a plurality of sensor elements in order to optimize the optical imaging behavior in the beam path. An active-optical element obtained here may be able if possible to correct (locally influence the light wavefront) further image defects (monochromatic and chromatic aberrations) in a static or dynamic fashion.

In order to generate actuation signals for the actuating components of the active-optical element or of the passive-optical element, it is necessary to acquire data from which the necessary dioptric power increase (=accommodation requirement) can be inferred.

Only acquiring the control signals of the diameter of the pupil does not suffice to determine the accommodation requirement since the measured variable depends on two influencing variables (the luminance and the distance of the object). One option for acquiring the data is to simultaneously measure the diameter of the pupil or the iris contraction/dilation movement and the luminance in the beam path in order to separate the pupillary near reaction from the pupillary light reflex.

The inventive use of the sensors, which are used as an implant, for detecting the pupil diameter affords the possibility of combining the measurement of the surrounding luminance and pupil diameter.

It is therefore advantageous to use a sensor or a plurality of sensors to measure the pupil diameter and the surrounding luminance within the scope of the integral artificial accommodation system because the pupil diameter decreases monotonically with increasing accommodation requirement (pupillary near reflex) and with increasing surrounding luminance (pupillary light reflex). Hence the pupil diameter and the surrounding luminance have to be measured to be able to determine the accommodation requirement using the pupillary near reflex.

The sensors which can be used according to the invention can comprise all suitable apparatuses for measuring the pupil diameter and surrounding luminance found in the prior art.

Every sensor comprises at least one sensor element. A sensor element is a light-sensitive area, e.g. a photodiode, photoresistor, phototransistor, CMOS (complementary metal oxide semiconductor) or CCD (charge coupled device) sensor element, which converts the incident photons into an analog or digital signal.

At least two sensor element are preferably used, one of which lies in the beam path, without being covered by the iris, for the purpose of measuring light (surrounding luminance), and at least one more which is wholly or partly covered by the iris in the region of the pupil edge and generates a signal for determining the diameter of the pupil from the shadowing through the iris.

The sensor elements are preferably arranged next to one another linearly to form a sensor element row with a width of preferably 1-500 µm, particularly preferably 10-50 µm. In the direction along the row, the individual sensor elements have a significantly smaller length of preferably 1 to 15 µm. Hence, the preferred maximum dimensions of a sensor element are 500×15 µm.

In contrast to the prior art, using sensors with said dimensions makes it possible for an implant to perform the described measurement. This therefore affords the possibility of using a preferably integral artificial accommodation system without a tactile or electric connection to the tissue. The option of having a single artificial accommodation system with only one implantation location, the capsular bag, significantly simplifies implantation. Since the system can perform measurements without an electrical or tactile connection to the body, it is possible to obtain a sufficiently accurate measurement which is independent of possibly occurring changes in the tissue.

The sensors can be used in a number of different embodiment variants:

One embodiment can consist of a linearly distributed sensor comprising a plurality of sensor elements being positioned in the implant behind the iris. The relevant sensor is able to detect the illumination strength incident on each sensor element. In the process, it must be ensured that at least one sensor element, which is preferably arranged centrally, is not covered by the iris under any circumstances. These sensor elements can determine the surrounding luminance.

The additional parts should be distributed such that at any one time at least one sensor element is partly covered by the pupil, or a change in the pupil diameter which is negligible relative to the pupillary near reflex leads to such a state; this should be independent of the pupil diameter, which in humans varies between 2 and 10 mm. If these sensor elements are very small, the number of sensor elements which are covered by the pupil and hence are unilluminated can be used directly to infer the pupil diameter. In the case of larger sensor elements, the pupil diameter can be inferred from the number of covered parts and the ratio of the illumination of the central part(s) to the partly illuminated sensor elements.

Preferably, at least one sensor element is provided to measure the surrounding luminance from the beam path of the eye which is not covered by the iris. In every pupil position, the pupil edge, and hence the pupil diameter, can be detected by at least one sensor element.

In order to compensate for positioning errors, three sensor elements for determining the pupil diameter are preferably arranged on different locations of the pupil edge in every iris position. Once there are at least three such elements, the pupil diameter can be reconstructed from the measurement signal even when the implant is decentered. The elements which do not lie centrally are preferably arranged on paths which extend radially outward from the optical axis and are rotationally symmetric.

Optionally, light which is incident through the pupil can also be deflected onto the sensor elements which are outside of the beam path. Means for deflecting the incident light onto the sensor arranged outside of the beam path can be provided in the beam path. Here, the means comprise a beam deflecting or guiding element in the beam path through the pupil. The relevant beam deflecting or guiding element in this case preferably comprises a reflection plane. This affords the possibility of also using larger sensors, which are an annoyance in the beam path, outside of the beam path. The described sensors afford the possibility of measuring the pupil diameter and the surrounding luminance from an implant. That is to say, according to the invention, use can be effected within the scope of an integral artificial accommodation system.

Within the scope of the invention described here, the data processing system is provided with the acquired data. However, the subject matter of the invention is also an above-described data acquisition system on its own, which can transmit measurement data to a receiver outside of the body for registering and further processing.

The acquired signals are processed by the data processing system (e.g. outlier tests, smoothing, filtering, amplifying). Features are extracted and classified using methods from classical statistics, computational intelligence and data mining in order to detect the accommodation intent. The required actuating signals for the optical system are generated using control and feedback control methods (e.g. fuzzy-controlled PID controller, adaptive control algorithms, learning algorithms). Both hierarchical control structures and central-decentral structures can be used.

An energy supply system, which may comprise an energy transducer, an energy storage device and a control unit, is used to supply the subsystems with energy. The energy transducer converts energy remotely transmitted from the outside (e.g. by inductive, capacitive or optical methods) or stored energy (e.g. battery, miniaturized fuel cell), which can also be available in the form of bodily fluids (e.g. the nutrient-rich aqueous humor, blood), or mechanical energy (e.g. from muscle movement) into electrical energy via an energy storage device. Said energy is emitted to the subsystems at precisely defined times by means of the control unit of the energy supply system.

By comparing the illumination strength measured by this sensor with a threshold value, the energy consumption of the overall system can be reduced in states in which accommodative capacity is unnecessary. That is to say that the system comprises an apparatus for switching to the low energy consuming stand-by state if the luminance falls below a threshold value. Once the threshold value is again exceeded, there is a switch into the operating state.

The overall system is implanted in the beam path using fixing elements which are suitable for axial fixing and radial centering. A number of haptical embodiments for intraocular lenses are known from ophthalmology. (Draeger, J.; Guthoff, R. F.: Kunstlinsenimplantation [Artificial lens implantations]. In: Augenheilkunde in Klinik and Praxis Band 4 [In Ophthalmology in clinics and in practice Volume 4] Eds.: Francois, J.; Hollwich, F. Georg Thieme Verlag Stuttgart New York (1991); Auffarth, G. U.; Apple, D. J.: Zur Entwicklungsgeschichte der Intraokularlinen [On the development history of intraocular lenses]. Ophthalmologe 98(11) (2001) 1017-1028). Said intraocular lenses are preferably secured in the iridocorneal angle, in the ciliary sulcus or in the capsular bag.

The artificial accommodation system is the technical part of a control system (closed-loop control system) which, as an artificial system, replaces the function of the naturally deformable eye lens and the ciliary muscle of a patient. The biological part basically consists of: the cornea, the aqueous humor and the vitreous humor as components of the dioptric apparatus; the retina as a natural sensor array; and the brain as natural data processing unit which generates control signals comprising data regarding the accommodation requirement.

The artificial accommodation system comprises an optical system with a variable focus and/or other optical properties. It forms a newly inserted component of the dioptric apparatus of the patient. It comprises a data acquisition system which optically obtains the diameter of the pupil and the luminance. A data processing system uses these measurements to determine the accommodation requirement and actuating signals for actuating the optical system are generated. The system is fed by a suitable energy supply system and is fixed in the patient's eye by means of a suitable fixing system.

The described accommodation system can be used to restore the accommodative capacity after the natural eye lens was removed due to a cataract or presbyopia.

DETAILED DESCRIPTION OF THE INVENTION

In the following text, the invention is described in more detail with reference to the figures.

Figure 1:
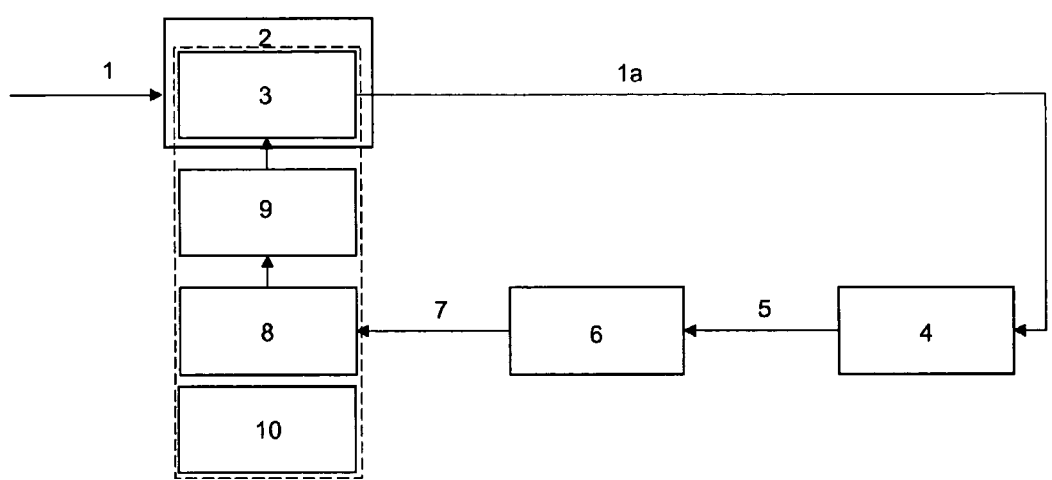
FIG. 1 shows a schematic diagram of the overall system.

FIG. 1 reproduces a schematic illustration of the overall system (artificial accommodation system). The data 1, e.g. light from an object whose object distance varies over time, passes through the dioptric apparatus of the human eye 2, which comprises the optical system 3. The focused light 1a impinges on the natural sensor—the retina 4.

The afferent signals 5 generated by the photoreceptors are supplied to the natural data processing system 6—the brain. From there, efferent signals 7 comprising data regarding the accommodation requirement are sent to motor-driven structures (e.g. the iris muscle, ciliary muscles, bulbus muscles). This data is picked up by the data acquisition system 8 of the artificial accommodation system. The data processing system 9 uses this to derive actuation signals for the optical system 3. Hence, the artificial accommodation system matches the dioptric power of the dioptric apparatus 2 to the accommodation requirement resulting from the temporally varying object distances. The energy supply system is represented by 10. All technical system components are framed by a dashed line.

Figure 2:
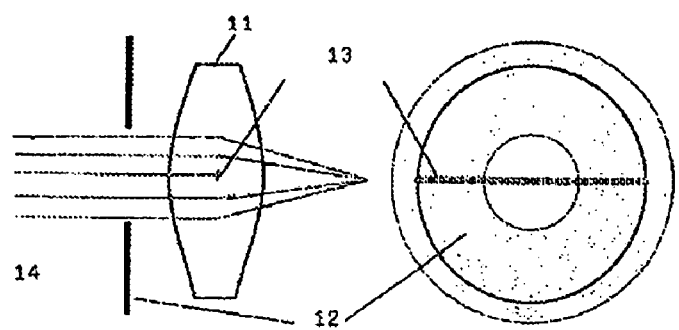
FIG. 2 schematically illustrates an option for applying the sensors.

FIG. 2 describes a schematic illustration of an option for applying the sensors according to the invention. In this case, the sensor 13 is positioned centrally in the implant 11, behind the iris 12. The sensor 13 can be used to measure the incident radiation 14. In order to be able to determine the surrounding luminance, it is absolutely necessary that at least one sensor element is not covered by the iris. In the process, the sensor element is preferably arranged centrally.

By contrast, the additional parts are arranged such that at least one sensor element is covered precisely in part by the pupil. The size of sensor elements is preferably selected to be so small that the pupil diameter can be inferred directly from the number of sensor elements that are covered by the pupil and hence are unilluminated. However, it is also possible to use larger sensor elements. In this case, the pupil diameter can be inferred from the number of the covered parts and from the ratios of the overall illumination to the partially illuminated sensor elements.

Figure 3:
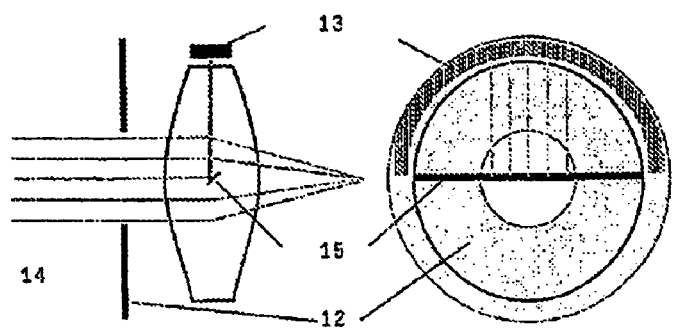
FIG. 3 schematically illustrates another embodiment.

FIG. 3 illustrates an application variant. According to this, it is possible to use mirrors 15 to deflect the light 14 entering through the pupils onto sensor elements 13 located outside of the beam path. In this case, larger sensors, which would otherwise be an annoyance in the beam path, can advantageously also be used.

The invention claimed is:

1. An implantable system for determining the accommodation requirement in an artificial accommodation system by optical measurement of the pupil diameter and the surrounding luminance, comprising
   a) at least one optical system,
   b) at least one data acquisition system which does not contact the ciliary muscle and has means for measuring a diameter of the pupil and luminance around at least one eye as a physical control signal for the accommodation requirement,
   c) at least one data processing system for generating an actuating signal for the optical system from the detected physical control signals or for the purpose of switching to the stand-by mode,
   d) at least one energy supply system, and
   e) at least one fixing system,
   wherein the system has one sensor or a plurality of sensors with sensor elements for measuring the pupil diameter and the surrounding luminance.

2. The system as claimed in claim 1, wherein the sensor elements comprise photosensitive sensor elements.

3. The system as claimed in claim 2, wherein the photosensitive sensor elements are photodiodes, photoreceptors, phototransistors, CCD or CMOS sensor elements.

4. The system as claimed in claim 1, wherein at least one sensor element is provided for measuring the surrounding luminance from the beam path of the eye not covered by the iris and the pupil edge and hence the pupil diameter can be detected by at least one sensor element in every pupil position.

5. The system as claimed in claim 4, wherein three sensor elements for determining the pupil diameter are arranged at different locations of the pupil edge in every iris position.

6. The system as claimed in claim 1, wherein the sensor elements, arranged next to one another to form at least one sensor element row, are composed to form at least one sensor.

7. The system as claimed in claim 6, wherein the sensor element rows in each case have a row height of 1-500 micrometers.

8. The system as claimed in claim 1, wherein the sensor is arranged in the beam path through the pupil.

9. The system as claimed in claim 8, wherein the sensor or the beam deflecting or beam guiding element is integrated into the optical system.

10. The system as claimed in claim 1, wherein means are provided in the beam path for deflecting the incident light onto the sensor arranged outside of the beam path.

11. The system as claimed in claim 10, wherein the means comprise a beam deflecting or beam guiding element in the beam path through the pupil.

12. The system as claimed in claim 11, wherein the beam deflecting or beam guiding element comprises a reflection plane.

\* \* \* \* \*

UNITED STATES PATENT AND TRADEMARK OFFICE
CERTIFICATE OF CORRECTION

PATENT NO.       : 8,403,483 B2
APPLICATION NO. : 12/449618
DATED            : March 26, 2013
INVENTOR(S)      : Klink et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 700 days.

Signed and Sealed this
First Day of September, 2015

Michelle K. Lee
*Director of the United States Patent and Trademark Office*